United States Patent [19]

Timmons et al.

[11] Patent Number: 4,559,941
[45] Date of Patent: Dec. 24, 1985

[54] EYEGLASS FRAME AND NASAL CANNULA ASSEMBLY

[76] Inventors: John W. Timmons; Gloria A. Timmons, both of 8390 W. Country Club, Sarasota, Fla. 33580

[21] Appl. No.: 564,186

[22] Filed: Dec. 22, 1983

[51] Int. Cl.⁴ .......................................... A61M 15/08
[52] U.S. Cl. ................................. 128/207.18; 351/158
[58] Field of Search ...................... 128/204.12, 206.18, 128/207.13, 207.18, 201.12; 351/66, 51, 52, 158; 81/3.5

[56] References Cited

U.S. PATENT DOCUMENTS

| | | |
|---|---|---|
| 2,168,705 | 8/1939 | Francisco et al. |
| 2,259,817 | 10/1941 | Hawkins. |
| 2,468,383 | 4/1949 | Tiffany. |
| 2,798,483 | 7/1957 | Kashima. |
| 2,954,027 | 9/1960 | Marasco. |
| 3,568,678 | 3/1971 | Pourquier. |
| 3,678,929 | 7/1972 | Buscher. |
| 3,682,171 | 8/1972 | Dali et al. |
| 3,726,275 | 4/1973 | Jackson et al. |
| 3,802,431 | 4/1974 | Farr. |
| 3,991,753 | 11/1976 | Viesca y Viesca. |
| 4,105,026 | 8/1978 | Hay, II. |
| 4,195,918 | 4/1980 | Freche ................................ 351/158 |

OTHER PUBLICATIONS

Thomas L. Petty, Louise M. Nett and S. Lakshmiranarayan, "A Single Nasal Prong for Continuous Oxygen Therapy", Respiratory Care, vol. 18, No. 4, Jul.-Aug. 1973, pp. 421-423.

Primary Examiner—Kyle L. Howell
Assistant Examiner—Daniel A. Haneiwich
Attorney, Agent, or Firm—Benjamin P. Reese, II

[57] ABSTRACT

An eyeglass frame and nasal cannula assembly for inconspicuously administering oxygen or other gases into the nostrils of a patient having respiratory ailments. An eyeglass frame has a pair of grooves in the rear surface of its front piece and a groove in the interior surface of each of its hinged temples. A nasal cannula assembly comprising a pair of cannula tubes is fitted in the grooves. One end of each of the cannula tubes is adapted for insertion in one nostril of the patient's nose and the opposite end of each of the cannula tubes is connected to a portable source of supply of oxygen or another gas to be administered to the patient. The overall appearance of the eyeglass frame is substantially identical to that of a conventional eyeglass frame and all but a small portion of the cannula tubes are hidden from view.

18 Claims, 7 Drawing Figures

U.S. Patent    Dec. 24, 1985    4,559,941
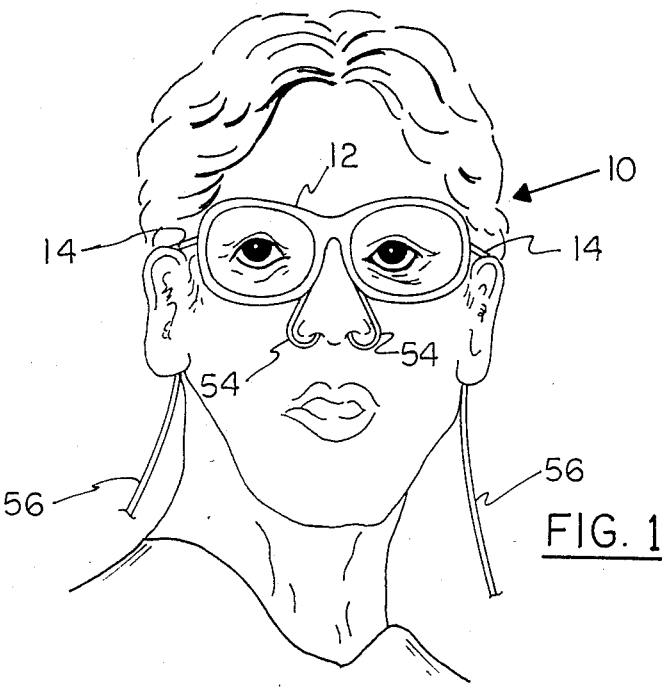
FIG. 1
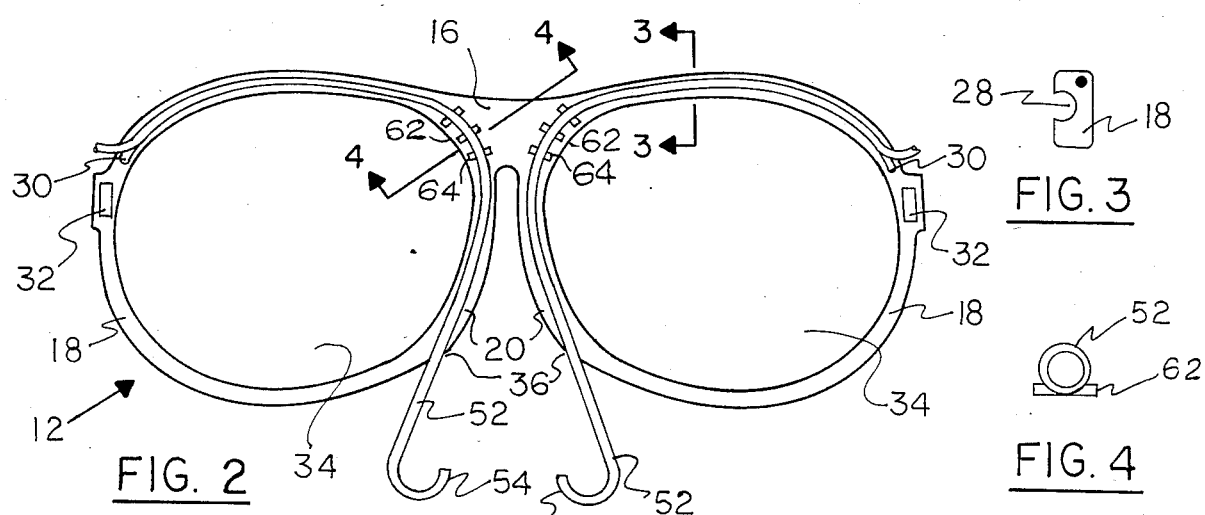
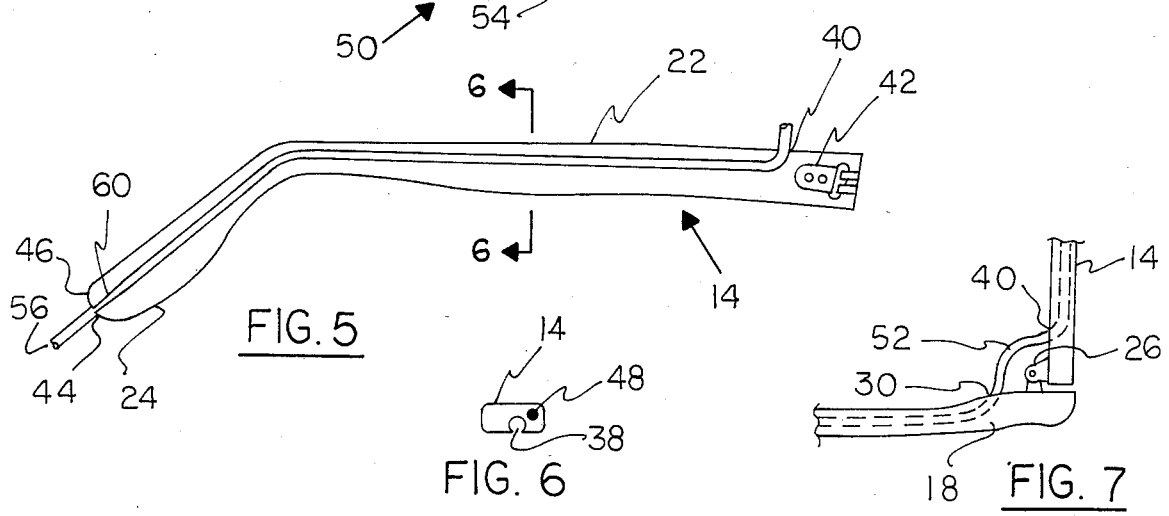

EYEGLASS FRAME AND NASAL CANNULA ASSEMBLY

BACKGROUND OF THE INVENTION

This invention relates generally to the administering of oxygen or other gases to a patient having respiratory ailments, and more particularly to an eyeglass frame and nasal cannula assembly for inconspicuously administering such gases into the nostrils of such a patient.

Certain respiratory ailments require the administering of oxygen or other gases to a patient over an extended period of time. Nasal cannula assemblies for administering oxygen or other gases to a patient having such respiratory ailments are well known in the prior art. However, the use of prior art nasal cannula assemblies in public can be embarrassing to many patients. Accordingly, many ambulatory patients who would otherwise be capable of dining in restaurants, attending plays, movies or sports events, visiting friends or relatives or otherwise participating in activities away from their homes will often confine themselves to their homes to avoid embarrassment.

Notwithstanding numerous developments relating to nasal cannula assemblies, it is not believed that the prior art provides a nasal cannula assembly for inconspicuously administering oxygen or other gases into the nostrils of a patient having respiratory ailments. Furthermore, it is not believed that the prior art provides an eyeglass frame and nasal cannula assembly. Yet, an eyeglass frame and nasal cannula assembly could be used for inconspicuously administering oxygen or other gases into the nostrils of a patient having respiratory ailments.

SUMMARY OF THE INVENTION

The present invention provides an eyeglass frame and nasal cannula assembly for inconspicuously administering oxygen or other gases into the nostrils of a patient having respiratory ailments.

The eyeglass frame of the present invention comprises a front piece and a pair of hinged temples. The rear surface of the front piece has a pair of identical grooves. A groove is provided along essentially the entire length of the interior surface of each of the temples. A nasal cannula assembly is fitted in the grooves in the rear surface of the front piece and the interior surfaces of the temples. Preferably, all of the grooves are undercut for retention to the nasal cannula assembly. Of course, the nasal cannula assembly could be retained by other means.

The nasal cannula assembly of the present invention preferably comprises a pair of identical cannula tubes, each of which is adjustably fitted in one of the grooves in the rear surface of the front piece and the groove in the interior surface of one of the temples. Each of the cannula tubes has a semi-circular portion on its lower end for insertion in one nostril of the patient's nose. The opposite ends of the cannula tubes are connected to a portable source of supply of oxygen or another gas to be administered to the patient. If desired, the patient can conceal the portable source of supply from view under a coat or other similar item of clothing.

These and many other advantages, features and objects of the present invention will be apparent from the following brief description of the drawings, description of the preferred embodiment and claims and the accompanying drawings.

BRIEF DESCRIPTION OF THE DRAWINGS

FIG. 1 is a front elevational view illustrating the appearance and position of the preferred embodiment of the eyeglass frame and nasal cannula assembly of the present invention in use.

FIG. 2 is a rear elevational view of the eyeglass frame and nasal cannula assembly with the temples of the eyeglass frame removed.

FIG. 3 is a sectional view of the front piece of the eyeglass frame taken along lines 3—3 in FIG. 2.

FIG. 4 is a sectional view of one of the two identical cannula tubes which comprise the nasal cannula assembly taken along lines 4—4 in FIG. 2.

FIG. 5 is a plan view of the interior surface of one of the temples of the eyeglass frame with one of the cannula tubes in position.

FIG. 6 is a sectional view of one of the temples of the eyeglass frame taken along lines 6—6 in FIG. 5.

FIG. 7 is a detail view illustrating the hinged connection between the front piece and one of the temples of the eyeglass frame with one of the cannula tubes in position.

DESCRIPTION OF THE PREFERRED EMBODIMENT

The preferred embodiment of the eyeglass frame and nasal cannula assembly of the present invention is illustrated in FIGS. 1-7.

Referring initially to FIG. 1, the eyeglass frame 10 which is illustrated comprises a front piece 12 and a pair of rearwardly extending, hinged temples 14. The general appearance of the eyeglass frame 10 is substantially identical to that of a typical conventional plastic eyeglass frame and may be varied to accommodate style changes and preferences. For example, various masculine and feminine models can be provided in a product line. Additionally, prescription lens can be used with the eyeglass frame 10 if desired.

Referring generally to FIGS. 2, 5 and 7, the general structure of the eyeglass frame 10 is also substantially identical to that of a typical conventional plastic eyeglass frame. Referring specifically to FIG. 2, the front piece 12 of the eyeglass frame 10 has a bridge 16 integrally formed with a pair of lens surrounding and retaining members 18. Preferably, each of the lens surrounding and retaining members 18 has an integrally formed nosepiece 20 as best illustrated in FIG. 2.

Referring specifically to FIG. 5, each of the temples 14 has an essentially straight, elongated portion 22 which extends rearward from the front piece 12 along the side of the patient's face and a downwardly curved portion 24 which fits behind the patient's ear to retain the eyeglass frame 10 in position. Referring specifically to FIG. 7, each of the temples 14 is connected to the front piece 12 by a hinge 26 in the conventional manner.

Returning to FIG. 2, the rear surface of the front piece 12 has a pair of identical undercut grooves 28. Each of the grooves 28 commences at a closed end 30 positioned near one of the hinged plates 32, follows the contour of the upper portion of the particular lens surrounding and retaining member 18, runs through the bridge 16, runs between the nosepiece 20 and lens opening 34, and terminates at an open end 36 positioned below the nosepiece 20. Each of the grooves 28 is essentially circular in cross-section as illustrated in FIG. 3.

Returning now to FIG. 5, each of the temples 14 has an undercut groove 38 which commences at a closed end 40 positioned near its hinge plate 42, runs along the length of the temple 14, and terminates at an open end 44 positioned at the tip 46 of the downwardly curved portion 24 of the temple 14. Each of the grooves 38 is essentially circular in cross-section as illustrated in FIG. 6. As further illustrated in FIG. 6, each of the temples 14 has a conventional interior stiffening wire 48.

As best illustrated in FIG. 2, the nasal cannula assembly 50 comprises a pair of identical cannula tubes 52. Each of the tubes 52 has a semi-circular portion 54 on its lower end for insertion in one of the nostrils of the patient's nose. Each of the tubes 52 is fitted in one of the grooves 28 in the rear surface of the front piece 12 as illustrated in FIG. 2 and the groove 38 in the interior surface of the adjacent temple 14 as illustrated in FIG. 5. A short portion of each of the tubes 52 spans the open space between the closed end 30 of the particular groove 28 and the closed end 40 of the particular groove 38 as illustrated in FIG. 7.

Referring to FIG. 4, each of the cannula tubes 52 has a small, rectangular member 62 bonded thereto. Alternatively, the rectangular member 62 can be integrally formed with the tubes 52 by a deformation or other suitable process. Each of the rectangular member 62 fits into one of the small, rectangular recesses 64 integrally formed with the grooves 28 in the bridge 16 of the front piece 12 which are illustrated in FIG. 2. Preferably, at least two recesses 64 are provided for each of the grooves 28 as illustrated in FIG. 2 to enable the patient to adjust the length of the nasal cannula assembly 50 for proper fit during use. The free or straight ends 56 of each of the tubes 52 are connected to a small bottle or other portable source of supply of oxygen or another gas to be administered to the patient. If desired, the portable source of supply can be concealed from view under a coat or other similar item of the patient's clothing. Finally, a pair of projections 60 over each of the grooves 38 near the tips 46 of the temples 14 lock the tubes 52 in position.

While the present invention has been disclosed in connection with its preferred embodiment, it should be understood that there may be other embodiments which fall within the scope and spirit of the invention as defined by the following claims.

We claim:

1. An eyeglass frame with a concealed nasal cannula assembly, comprising:
    (a) an eyeglass frame having a front piece and a pair of hinged temples, said front piece having a groove in its rear surface; and
    (b) a nasal cannula assembly fitted in said groove.

2. An eyeglass frame with a concealed nasal cannula assembly as recited in claim 1, wherein said nasal cannula assembly is a cannula tube having a semi-circular portion on its lower end for insertion in one nostril of the patient's nose.

3. An eyeglass frame with a concealed nasal cannula assembly as recited in claim 2, wherein said groove is undercut.

4. An eyeglass frame with a concealed nasal cannula assembly as recited in claim 1, wherein one of said temples has a groove in its interior surface and said nasal cannula assembly is fitted in said groove in the rear surface of said front piece and said groove in the interior surface of said temple.

5. An eyeglass frame with a concealed nasal cannula assembly as recited in claim 4, wherein said nasal cannula assembly is a cannula tube having a semi-circular portion on its lower end for insertion in one nostril of the patient's nose.

6. An eyeglass frame with a concealed nasal cannula assembly as recited in claim 5, wherein said grooves are undercut.

7. An eyeglass frame with a concealed nasal cannula assembly, comprising:
    (a) an eyeglass frame having a front piece and a pair of hinged temples, said front piece having a pair of grooves in its rear surface; and
    (b) a nasal cannula assembly fitted in said grooves.

8. An eyeglass frame with a concealed nasal cannula assembly as recited in claim 7, wherein said nasal cannula assembly comprises a pair of identical cannula tubes, each of said cannula tubes having a semi-circular portion on its lower end for insertion in one nostril of the patient's nose, and each of said cannula tubes being fitted in one of said grooves.

9. An eyeglass frame with a concealed nasal cannula assembly as recited in claim 8, wherein said grooves are undercut.

10. An eyeglass frame with a concealed nasal cannula assembly as recited in claim 7, wherein each of said temples has a groove in its interior surface and said nasal cannula assembly is fitted in said grooves in the rear surface of said front piece and said grooves in the interior surfaces of said temples.

11. An eyeglass frame with a concealed nasal cannula assembly as recited in claim 10, wherein said nasal cannula assembly comprises a pair of identical cannula tubes, each of said cannula tubes having a semi-circular portion on its lower end for insertion in one nostril of the patient's nose, and each of said cannula tubes being fitted in one of said grooves in the rear surface of said front piece and one of said grooves in the interior surfaces of said temples.

12. An eyeglass frame with a concealed nasal cannula assembly as recited in claim 11, wherein said grooves are undercut.

13. An eyeglass frame with a concealed cannula assembly comprising:
    (a) and eyeglass frame having a front piece and a pair of hinged temples, said front piece having a pair of lens surounding and retaining members separated by an integrally formed bridge, each of said lens surrounding and retaining members having an integrally formed nosepiece, and a pair of grooves in its rear surface, each of said grooves commencing near one of said hinged temples, following the contour of the upper portion of one of said lens surrounding and retaining members, and terminating below said nosepieces, and each of said temples having an elongated portion, a downwardly curved portion and a groove in its interior surface, said groove commencing near said front piece, running along the length of said elongated portion and said downwardly curved portion, and terminating at the tip of said downwardly portion;
    (b) a pair of identical cannula tubes, each of said cannula tubes having a semi-circular portion on its lower end for insertion in one nostril of the patient's nose, and each of said cannula tubes being fitted in one of said grooves in the rear surface of said front piece and one of said grooves in the interior surfaces of said temples; whereby the portions of said tubes fitted in said grooves are concealed.

14. An eyeglass frame with a concealed nasal cannula assembly as recited in claim 13, wherein said grooves are undercut.

15. An eyeglass frame with a concealed nasal cannula assembly as recited in claim 13, further comprising a rectangular recess integrally formed with each of said grooves in the rear surface of said front piece and a rectangular member bonded to or integrally formed with each of said cannula tubes, each of said rectangular recesses being adapted for receipt of one of said rectangular members.

16. An eyeglass frame with a concealed nasal cannula assembly as recited in claim 15, wherein said grooves are undercut.

17. An eyeglass frame with a concealed nasal cannula assembly as recited in claim 13, further comprising a plurality of rectangular recesses integrally formed with each of said grooves in the rear surface of said front piece and a rectangular member bonded to each of said cannula tubes, each of said rectangular recesses being adapted for receipt of one of said rectangular members.

18. An eyeglass frame with a concealed nasal cannula assembly as recited in claim 17, wherein said grooves are undercut.

* * * * *